US012283026B2

(12) United States Patent
Yoshikawa

(10) Patent No.: US 12,283,026 B2
(45) Date of Patent: Apr. 22, 2025

(54) ULTRASOUND IMAGING APPARATUS, SIGNAL PROCESSING METHOD, AND SIGNAL PROCESSING PROGRAM

(71) Applicant: FUJIFILM Healthcare Corporation, Kashiwa (JP)

(72) Inventor: Hideki Yoshikawa, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 429 days.

(21) Appl. No.: 17/835,218

(22) Filed: Jun. 8, 2022

(65) Prior Publication Data

US 2022/0414836 A1    Dec. 29, 2022

(30) Foreign Application Priority Data

Jun. 28, 2021  (JP) .................... 2021-106754

(51) Int. Cl.
*G06T 5/70* (2024.01)
*A61B 8/00* (2006.01)
(Continued)

(52) U.S. Cl.
CPC ............ *G06T 5/70* (2024.01); *A61B 8/06* (2013.01); *A61B 8/4494* (2013.01);
(Continued)

(58) Field of Classification Search
CPC .... G06T 5/70; G06T 5/20; G06T 5/50; G06T 2207/10132; G06T 2207/20216;
(Continued)

(56) References Cited

U.S. PATENT DOCUMENTS

2022/0096055 A1* 3/2022 Di Ianni ............. A61B 8/5223

FOREIGN PATENT DOCUMENTS

JP    2019-054938    4/2019
JP    2019-103919 A    6/2019
(Continued)

OTHER PUBLICATIONS

Mauldin, F.W., Lin, D. and Hossack, J.A., 2011. The singular value filter: A general filter design strategy for PCA-based signal separation in medical ultrasound imaging. IEEE transactions on medical imaging, 30(11), pp. 1951-1964.*
Demené, C., Deffieux, T., Pernot, M., Osmanski, B.F., Biran, V., Gennisson, J.L., Sieu, L.A., Bergel, A., Franqui, S., Correas, J.M. and Cohen, I., 2015. Spatiotemporal clutter filtering of ultrafast ultrasound data highly increases Doppler and fUltrasound sensitivity. IEEE transactions on medical imaging, 34(11).*
(Continued)

*Primary Examiner* — Zhitong Chen
(74) *Attorney, Agent, or Firm* — Paul Teng

(57) ABSTRACT

The invention provides an ultrasound imaging apparatus capable of highly accurately extracting a blood flow in a fine blood vessel in a short time. N pieces of frame data is generated by receiving ultrasound waves reflected by a subject with a plurality of transducers. A correlation matrix is generated based on a vector in which data at a corresponding position of the frame data is arranged for N frames, and a singular value and a singular vector for each of N ranks are calculated. A first filter element is calculated based on a variance between data at a corresponding position zx among a plurality of blood flow component frame data obtained by multiplying a plurality of the frame data by singular vectors at a threshold rank k or more. The second filter element is calculated based on the tissue component frame data obtained by multiplying the frame data by a singular vector at a rank 1. The frame data is weighted by the first filter element and/or the second filter element to generate a clutter reducing image.

14 Claims, 10 Drawing Sheets

(51) Int. Cl.
  *A61B 8/06* (2006.01)
  *G06T 5/20* (2006.01)
  *G06T 5/50* (2006.01)
  *G06V 10/74* (2022.01)

(52) U.S. Cl.
  CPC .......... *A61B 8/5223* (2013.01); *A61B 8/5269* (2013.01); *G06T 5/20* (2013.01); *G06T 5/50* (2013.01); *G06V 10/761* (2022.01); *G06T 2207/10132* (2013.01); *G06T 2207/20216* (2013.01); *G06T 2207/30104* (2013.01)

(58) Field of Classification Search
  CPC ............ G06T 2207/30104; A61B 8/06; A61B 8/4494; A61B 8/5223; A61B 8/5269; A61B 8/463; A61B 8/0891; A61B 8/52; G06V 10/761; G01S 7/52026; G01S 15/8915; G01S 15/8981
  See application file for complete search history.

(56) References Cited

FOREIGN PATENT DOCUMENTS

| | | | | |
|---|---|---|---|---|
| JP | 2020036774 A | * | 3/2020 | ........... A61B 8/5207 |
| JP | 2020-185122 | | 11/2020 | |

OTHER PUBLICATIONS

Baranger, J., Arnal, B., Perren, F., Baud, O., Tanter, M. and Demené, C., 2018. Adaptive spatiotemporal SVD clutter filtering for ultrafast Doppler imaging using similarity of spatial singular vectors. IEEE transactions on medical imaging, 37(7), pp. 1574-1586.*

Japanese official action dated Dec. 26, 2023 (and English translation thereof) in connection with Japanese Patent Application No. 2021-106754.

* cited by examiner

FIG. 7A
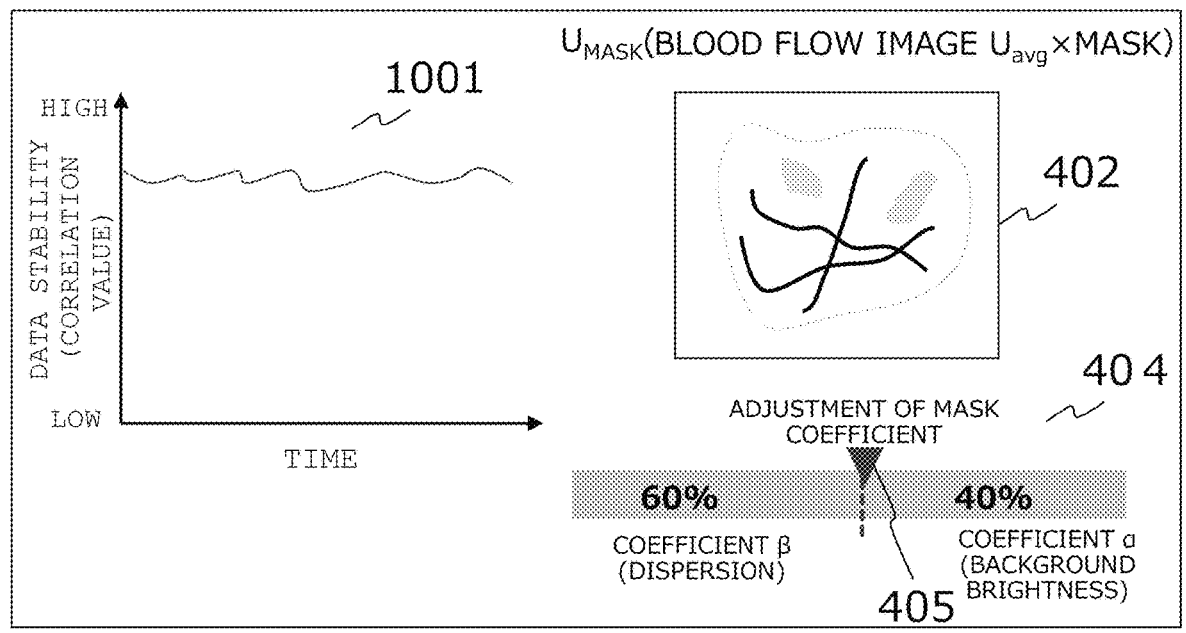
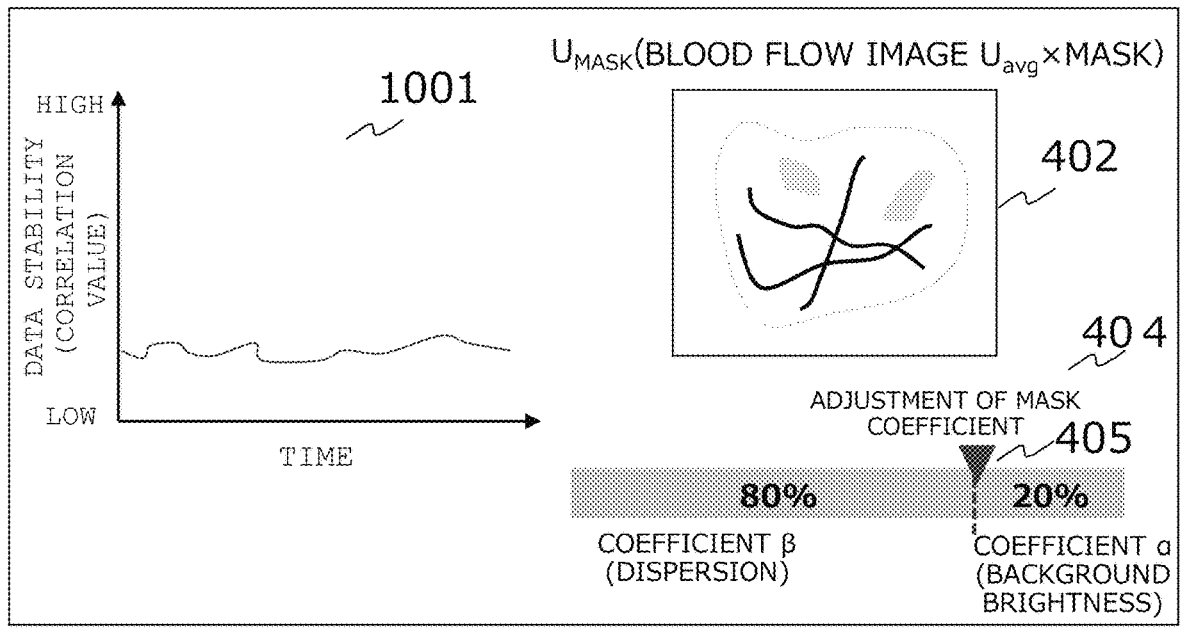
FIG. 7B

ULTRASOUND IMAGING APPARATUS, SIGNAL PROCESSING METHOD, AND SIGNAL PROCESSING PROGRAM

BACKGROUND OF THE INVENTION

1. Field of the Invention

The present invention relates to an ultrasound imaging apparatus, and relates to a technique for reducing a clutter component derived from a tissue in a technique for acquiring a blood flow image in a living body using singular value decomposition.

2. Related Art

An ultrasound imaging apparatus is widely used as a medical inspection apparatus that presents invisible information in a living body in the form of numerical values or images. As a basic imaging method, an ultrasound signal (echo signal) is transmitted toward an imaged object in the living body, and amplitude information of the receive signals obtained by reflection is used to display a morphology of a tissue. On the other hand, a technique of imaging a position and a velocity of a blood flow by measuring a phase change based on a Doppler effect is also widely known.

In recent years, as in JP-A-2019-54938 and JP-A-2020-185122, a blood flow imaging technique based on a principal component analysis has been developed, and a technique for displaying a fine blood vessel network as image information attracts attention. The principal component analysis is a statistical analysis method based on analysis methods for singular value decomposition and eigenvalue decomposition. When the principal component analysis is applied to the ultrasound signal, information (for example, components having a relatively high brightness such as a boundary and parenchyma of a tissue) that well reproduces an original image is classified as a higher order principal component. On the contrary, information (for example, dynamic blood flow component having a lower reflectance than a tissue) having a low information dominance ratio is classified into a lower order principal component. A technique has been proposed in which a blood flow component is specifically extracted from the ultrasound signal and imaged by utilizing this characteristic.

A technique disclosed in JP-A-2019-54938 is a method for improving a quality of blood flow images by executing the principal component analysis on an acquired ultrasound signal (Doppler signal) and reducing a component (clutter component) derived from a tissue movement due to a change in a body position, breathing, a heartbeat, or the like. For example, a main filter matrix is calculated such that a first principal component to a third principal component are removed and a fourth principal component to a sixth principal component are maintained. The first to third principal components correspond to the clutter component. The fourth to sixth principal components correspond to the blood flow component. By applying the main filter matrix to the Doppler signal, an image in which the clutter component is reduced is generated. Further, the first principal component and the sixth principal component are extracted from the Doppler signal, and a ratio of the first principal component and the sixth principal component is used as an index to weight a power signal of the blood flow. Accordingly, a residual clutter component is adaptively reduced.

A technique disclosed in JP-A-2020-185122 is a technique of reducing the clutter component by adjusting signal strength of a displayed image based on information obtained by the principal component analysis of the ultrasound signal.

SUMMARY OF THE INVENTION

In recent years, an ultrasound imaging apparatus capable of highly accurately extracting the blood flow in a fine blood vessel has been desired. Therefore, inventors have focused on that clutter of a background image and a pixel of a blood vessel wall, which tends to have a high brightness, are required to be reduced more than in the related art. Although the principal component analysis based on the singular value decomposition and the eigenvalue decomposition is an effective method for extracting a fine blood vessel structure, reduction of the clutter component may be insufficient depending on a speed of the movement of the tissue and the blood flow, or a magnitude of a brightness. In that case, the clutter component remains in the displayed image, and an accurate blood vessel structure cannot be visually recognized, resulting in a decrease in diagnostic accuracy and an increase in a stress in an interpretation.

In the technique described in JP-A-2019-54938, a first specific principal component (for example, the first principal component) and a second specific principal component (for example, the sixth principal component) are extracted from the Doppler signal according to the principal component analysis, and a ratio of the first specific principal component and the second specific principal component is used as an index to adjust (weight) the brightness. For example, when the ratio of the sixth principal component to the first principal component is used as an index, the index is close to 1 if a pixel is located in the blood vessel, and the index is close to 0 if the pixel is located in an organ tissue.

However, for example, when the organ tissue contains a high brightness component, or when the organ tissue moves violently and information on the tissue and the blood flow is dispersed in a wide range of principal components, even if the pixel is located in the organ tissue, the index is not 0 but a relatively high value. As a result, it may not be possible to reduce residual clutter.

On the other hand, in the technique described in JP-A-2020-185122, the principal component analysis is executed on acquired time-series ultrasound signals, a brightness adjustment amount is calculated based on a result of the principal component analysis, and a brightness of the displayed image is adjusted. That is, the technique is a method for calculating the residual clutter component based on acquired ultrasound signal data. However, since the ultrasound signal also contains the blood flow component, not only the residual clutter but also the blood flow component may be excessively reduced, and as a result, visibility of the blood vessel may be impaired.

In general, when clutter reduction is performed according to the principal component analysis, an effect of the clutter reduction can be improved by executing a large number of times of transmission and reception, obtaining a large number of ultrasound signals (Doppler signals), and executing the principal component analysis. However, it takes time to execute the transmission and reception, and real-time performance deteriorates.

An object of the invention is to provide an ultrasound imaging apparatus capable of highly accurately extracting a blood flow in a fine blood vessel in a short time.

According to the invention, the following ultrasound imaging apparatus is provided.

That is, the ultrasound imaging apparatus according to the invention includes a data collection unit, a matrix conversion unit, a matrix analysis unit, a filter element generation unit, and an image processing unit. The data collection unit receives a plurality of receive signals obtained by receiving, with an array in which a plurality of transducers are arranged in an x direction, ultrasound waves reflected sequentially in a depth z direction of a subject to which the ultrasound waves are transmitted. The data collection unit repeats processing of generating frame data by arranging the received receive signals on a zx plane, and generates the frame data for N frames. The matrix conversion unit generates a correlation matrix based on a vector in which data at a corresponding position zx of the frame data is arranged for N frames. The matrix analysis unit performs singular value decomposition of the correlation matrix processing and calculates a singular vector for each of N ranks of the receive signals. The filter element generation unit generates at least one of a first filter element and a second filter element as a filter element. The image processing unit uses the filter element generated by the filter element generation unit to weight the frame data or a pixel value of an image generated based on the frame data and generate a clutter reducing image. The first filter element is calculated based on a variance between data at the corresponding position zx among a plurality of blood flow component frame data obtained by multiplying a plurality of the frame data by a plurality of singular vectors in a predetermined rank range of a preset threshold rank k or more. The second filter element is calculated based on tissue component frame data obtained by multiplying one or more of the frame data by a singular vector at a predetermined rank less than the threshold rank k.

According to the invention, a clutter component derived from a tissue can be effectively reduced in a short time according to a principal component analysis, and a blood flow in a fine blood vessel can be highly accurately extracted.

BRIEF DESCRIPTION OF THE DRAWINGS

FIGS. 7A and 7B are views showing examples of a display screen of the ultrasound imaging apparatus according to the second embodiment;

DESCRIPTION OF EMBODIMENTS

Ultrasound imaging apparatuses according to embodiments of the invention will be described with reference to the drawings.

First Embodiment

Figure 1:
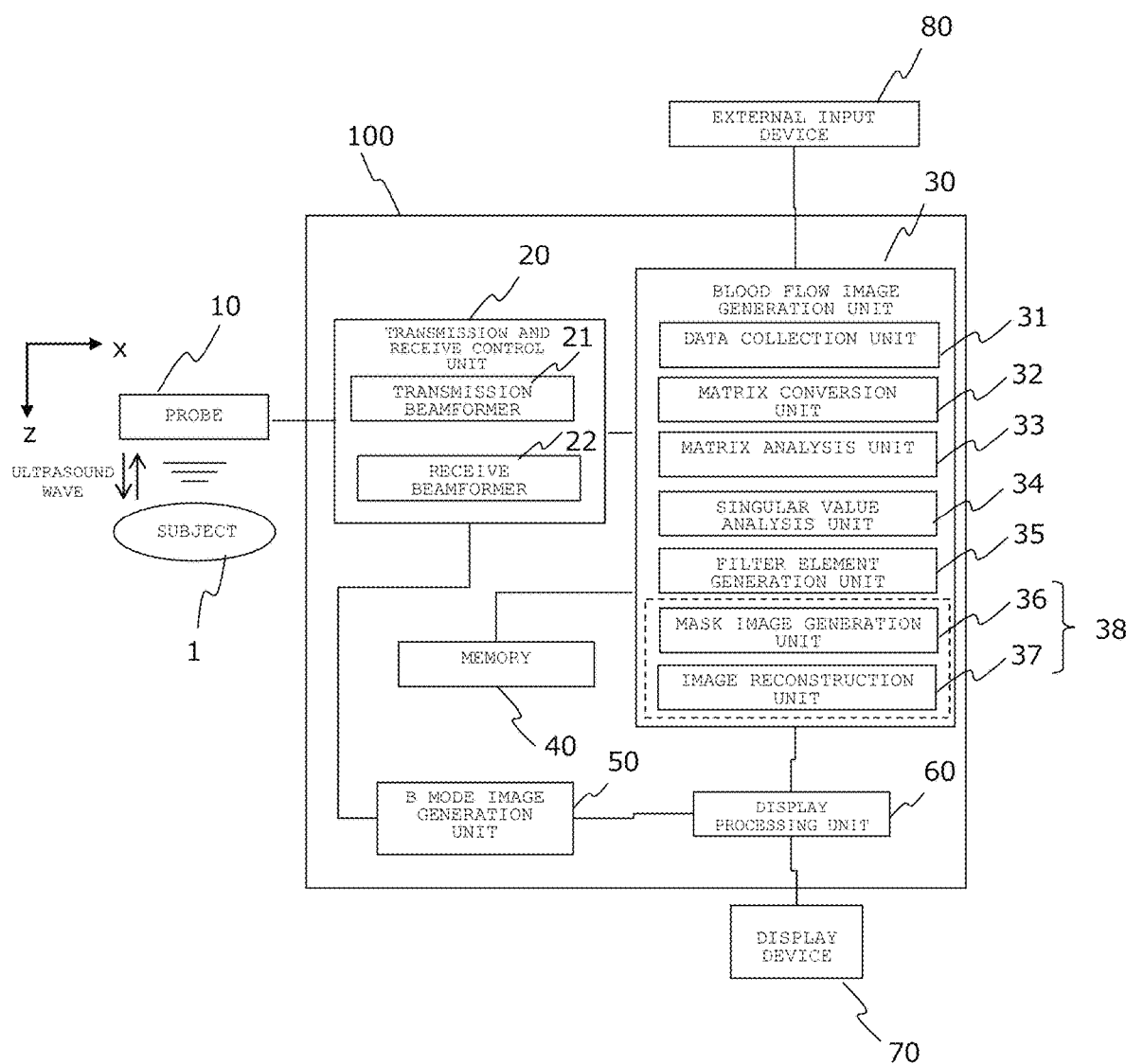
FIG. 1 is a block diagram of an ultrasound imaging apparatus according to a first embodiment.
Figure 2:
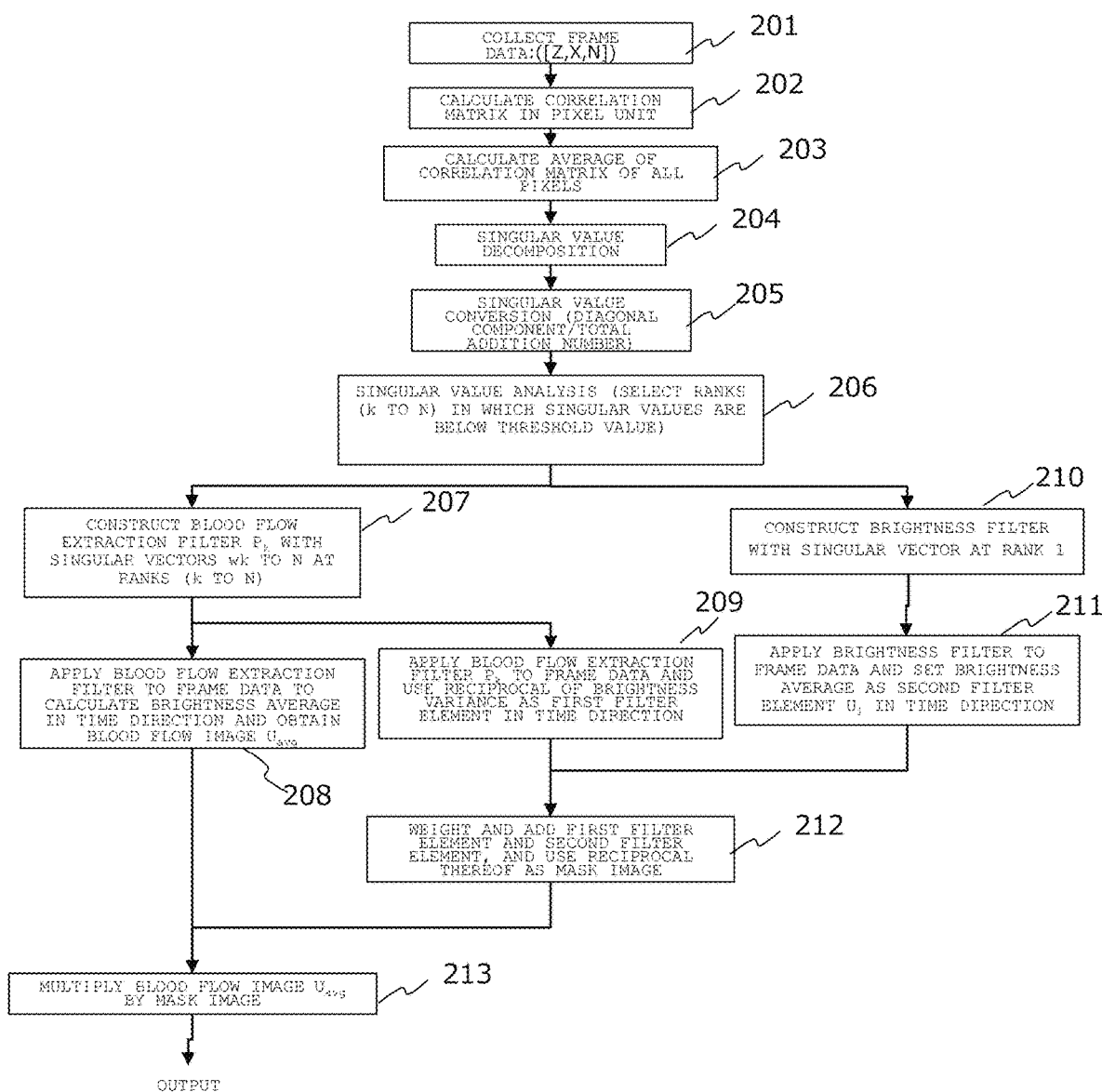
FIG. 2 is a flowchart showing processing executed by a blood flow image generation unit 30 of the ultrasound imaging apparatus according to the first embodiment.
Figure 3:
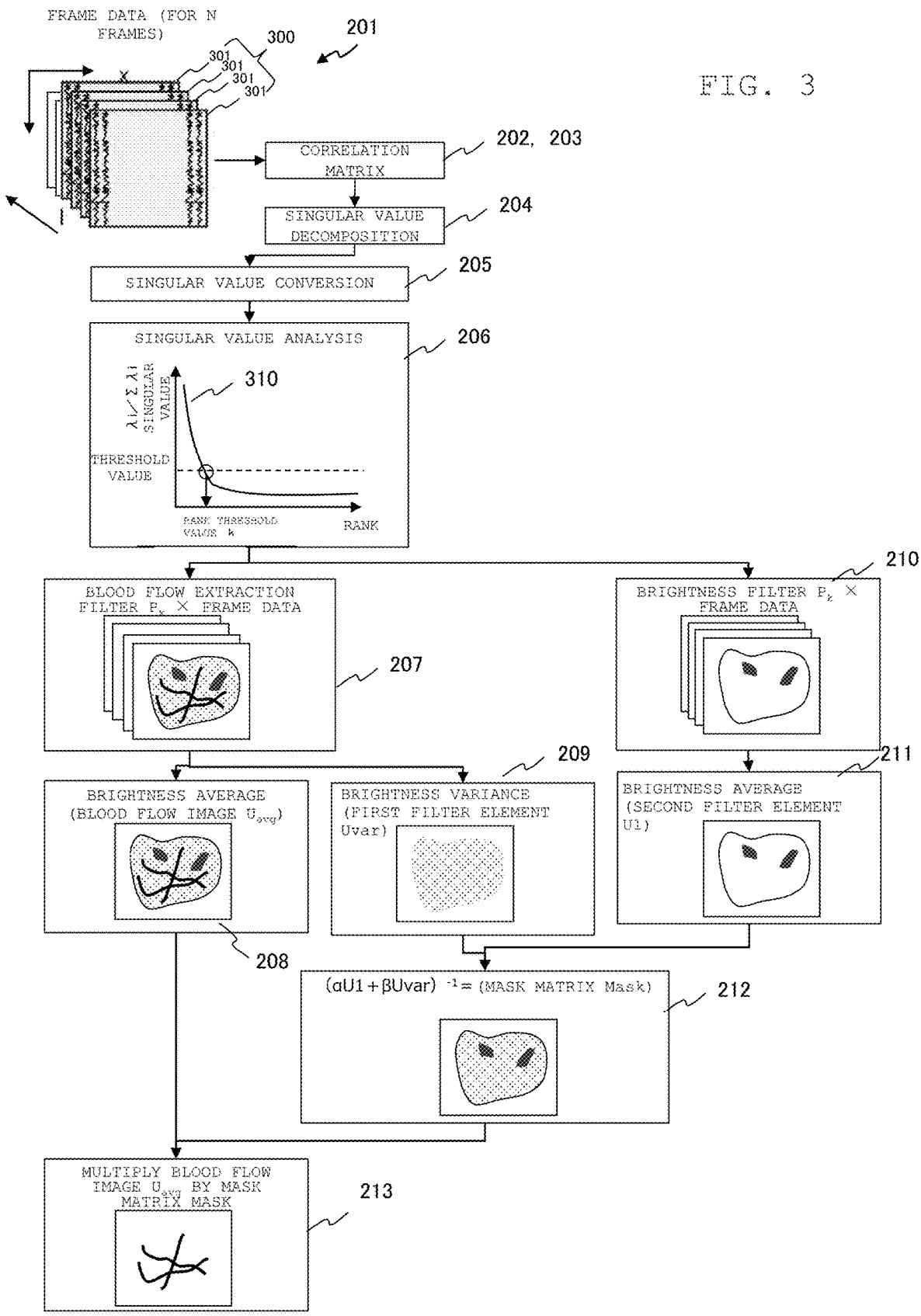
FIG. 3 is a flowchart illustrating the processing in FIG. 2 with figures and graphs.

An ultrasound imaging apparatus 100 according to a first embodiment will be described with reference to FIGS. 1 to 3. FIG. 1 is a diagram showing a schematic configuration of the ultrasound imaging apparatus according to the first embodiment, and FIG. 2 is a flowchart showing processing executed by a blood flow image generation unit of the ultrasound imaging apparatus. FIG. 3 is a flowchart illustrating the processing in FIG. 2 with figures and graphs.

The configuration of the ultrasound imaging apparatus 100 according to the first embodiment will be described with reference to FIG. 1. The ultrasound imaging apparatus 100 is connected to a probe 10, an external input device 80 that receives an instruction from an outside, and a display device 70. The probe 10 includes an array in which ultrasound transducers are arranged in an x direction. Each transducer includes a piezoelectric element and the like.

The ultrasound imaging apparatus 100 includes a transmission and receive control unit 20, a blood flow image generation unit 30, a memory 40, a B mode image generation unit 50, and a display processing unit 60.

The transmission and receive control unit 20 includes a transmission beamformer 21, a receive beamformer 22, and an orthogonal detector (not shown). The transmission beamformer 21 generates transmission signals, outputs the transmission signals to the transducers of the probe 10, and transmits the transmission signals in a depth direction (z direction) of a subject 1. The receive beamformer 22 receives receive signals that are output by the transducers of the probe 10 after the transducers receive ultrasound waves, for example, reflected by the subject 1, executes predetermined phasing processing, and generates receive beam data. The orthogonal detector orthogonally detects the receive beam data and generates beam data as a complex signal.

The blood flow image generation unit 30 includes a data collection unit 31, a matrix conversion unit 32, a matrix analysis unit 33, a singular value analysis unit 34, a filter element generation unit 35, a mask image generation unit 36, and an image reconstruction unit 37. The mask image generation unit 36 and the image reconstruction unit 37 constitute an image processing unit 38.

The blood flow image generation unit 30 is implemented by a computer including a processor such as a central processing unit (CPU) or a graphics processing unit (GPU) and a memory, and the processor reads and executes a program stored in the memory in advance to implement functions of the units 31 to 38 by software. The blood flow image generation unit 30 may be partially or wholly implemented by hardware. For example, a custom IC such as an application specific integrated circuit (ASIC) or a programmable IC such as a field-programmable gate array (FPGA) may be used to design a circuit so as to implement the functions of the units 31 to 38.

Hereinafter, operations of the units of the ultrasound imaging apparatus 100 according to the present embodiment will be described.

The transmission beamformer 21 outputs the transmission signals to which a predetermined time delay is applied to the transducers of the probe 10. Accordingly, the transducers of the probe 10 irradiate, with the ultrasound waves, an organ tissue in a living body (subject 1) to be imaged by electroacoustic conversion or the like based on a piezoelectric effect. The ultrasound waves propagate in the living body so as to focus at a predetermined depth. In a process of the propagation, the ultrasound waves repeat reflection at interfaces having different acoustic impedances.

The reflected waves (ultrasound waves) reach the transducers of the probe 10 again, are received, and are converted into the receive signals (electrical signals). The receive beamformer 22 executes the phasing processing on the receive signals so as to return the time delay set at the time of transmission, and generates, in the x direction, a plurality of receive beam data in the depth z direction. The receive signals after the phasing processing is sent to the blood flow image generation unit 30. However, as long as the receive signals treated in the invention are signals obtained by the reflection from an imaged target, a transmission and reception method thereof is not particularly limited, and for example, a signal obtained by transmitting a plane wave to an imaged target without applying a time delay to the transducers of the probe 10 may be used.

When the blood flow image generation unit 30 generates a blood flow image, the ultrasound waves are repeatedly transmitted and received N times to and from the same imaging surface of the subject 1.

Next, processing executed by the units 31 to 38 of the blood flow image generation unit 30 will be described with reference to the flowcharts in FIGS. 2 and 3.

Step 201

The data collection unit 31 receives a plurality of receive beam data after executing the phasing by the receive beamformer 22, arranges the received receive beam data on a zx plane, and generates frame data 301. The data collection unit 31 receives a signal each time the ultrasound waves are transmitted and received N times by the probe 10 in the same imaging range, and acquires the frame data 301 for N frames. The data collection unit 31 stores time-series (N pieces of) frame data 301 in the memory 40 in the form of an in-phase/quadrature-phase (IQ) signal. Accordingly, as shown in step 201 in FIG. 3, three-dimensional data 300 arranged in x, z, and N directions is stored in the memory 40.

A quantity of the ultrasound waves reflected by a blood flow in the subject 1 is small, and most of the ultrasound waves are reflected at an interface of the structure in the subject 1. Therefore, most of the frame data 301 is a background component (clutter component) reflected by the structure, and a proportion of the blood flow component is fairly small. Therefore, the clutter component of the frame data 301 is removed and reduced by the following processing, and the blood flow component is extracted.

Step 202

The matrix conversion unit 32 extracts data $u_{zxi}$ of one pixel (position zx) of the frame data 301 from corresponding pixels (position zx) of the N pieces of frame data 301, and generates a vector $u_{zx}$ as indicated in an equation (1) by arranging the data for N frames. Here, i denotes a frame data number in the N direction. The vector $u_{zx}$ is ensemble data of singular value decomposition.

Further, a correlation matrix $R_{zx}$ is generated using the vector $u_{zx}$ according to an equation (2).

$$u_{zx}=[u_{zx1}, \ldots ,u_{zxN}]^T \quad (1)$$

$$R_{zx}=u_{zx}u^H_{zx} \quad (2)$$

Step 203

The matrix conversion unit 32 obtains the correlation matrix $R_{zx}$ for each of a plurality of pixels (for example, all pixels), averages the obtained correlation matrices according to an equation (3), and calculates an average correlation matrix $\overline{R}$ (Here, "–" in $R^-$ denotes "–" above the letter R in the equation (3)).

$$\overline{R} = \frac{1}{XZ}\sum_{z=1}^{Z}\sum_{x=1}^{X}R_{zx} \quad (3)$$

Step 204

The matrix analysis unit 33 calculates, based on the average correlation matrix $\overline{R}$ obtained by the matrix conversion unit 32, a singular value $\lambda_i$ and a singular vector $w_i$ (i=1, 2, . . . , N) for each rank i, that is, the first principal component to the Nth principal component according to an equation (4). (Here, the rank i denotes the number of each principal component obtained according to a principal component analysis based on the singular value decomposition, the first principal component corresponding to a higher order is called a rank 1 principal component, and the Nth principal component is called a rank N principal component). The equation (4) is a calculation process for the principal component analysis, but when the frame data 301 is a square matrix, eigenvalue decomposition may be used as an alternative method.

$$\overline{R} = W\Lambda W^H = \sum_{i=1}^{N}\lambda_i w_i w_i^H \quad (4)$$

Steps 205 and 206

Next, the singular value analysis unit 34 determines a threshold rank for separating a principal component of the blood flow component and a principal component of the clutter component by utilizing the fact that the blood flow component contained in the receive signals is significantly lower than the clutter component.

The singular value analysis unit 34 calculates the singular value $\lambda_i$ (a diagonal component of a matrix $\Lambda$) of each principal component calculated by the singular value decomposition. Specifically, $\lambda_i/\Sigma\lambda_i$ is obtained by dividing the singular value $\lambda_i$ by a total addition number ($\Sigma\lambda_i$) of the singular value $\lambda_i$ (step 204). $\lambda_i/\Sigma\lambda_i$ indicates how much each principal component contributes to reproduction of original data, that is, the information dominance ratio.

A graph 310 having $\lambda_i/\Sigma\lambda_i$ as a vertical axis and the rank i (i=1 to N) as a horizontal axis is generated as shown in step 205 in FIG. 3. Subsequently, a rank (rank threshold value k) of a principal component corresponding to a predetermined threshold value of $\lambda_i/\Sigma\lambda_i$ is selected. An example of the threshold value of $\lambda_i/\Sigma\lambda_i$ is 0.01, which follows that an amount of energy of the blood flow component with respect to a tissue component is approximately 1%.

A preset value may be used as the rank threshold value k.

Steps 207 and 208

The singular vector ($w_i$, i=k to N) below a rank threshold value (ranks k to N) can serve as a filter that reduces the clutter component contained in the receive signals and that extracts the blood flow component. The image reconstruction unit 37 uses the singular vector to reconstruct the blood flow image which is extracted the blood flow component.

Specifically, the image reconstruction unit 37 generates a sum of products of a plurality of singular vectors and singular values in a predetermined rank range of the threshold ranks k to N as a blood flow extraction filter $P_k$ according to an equation (5) (step 207).

Next, the image reconstruction unit 37 obtains blood flow component frame data $U\hat{}$ by multiplying the plurality of frame data 301 (for example, three-dimensional data U which is all of frame data 301) by the blood flow extraction filter $P_k$ according to equations (6) and (7). (Here, "^" in $U\hat{}$ denotes "^" above the letter U in the equation (6)).

Further, the image reconstruction unit 37 generates a blood flow image $U_{avg}$ by adding and averaging the obtained three-dimensional data (N pieces of frame data) $U\hat{}$ for each pixel (position zx) in a time axis direction (N direction) according to an equation (8) (step 208).

$$P_k = W\Lambda^{(k)}W^H| = \sum_{i=k}^{N} \lambda_i w_i w_i^H \quad (5)$$

$$\hat{U} = P_k U \quad (6)$$

$$U = \begin{bmatrix} \vdots \\ \cdots & u_{zx} & \cdots \\ \vdots \end{bmatrix} \quad (7)$$

$$U_{avg} = avg[\hat{U}] \quad (8)$$

Steps 209 to 211

The filter element generation unit 35 generates at least one of a first filter element and a second filter element as a filter element. In the present embodiment, both the first filter element and the second filter element are calculated.

First Filter Element

The first filter element is calculated based on a variance between data at the corresponding position zx among a plurality of blood flow component frame data. The plurality of blood flow component frame data are obtained by multiplying the plurality of frame data 301 by a plurality of singular vectors ($w_i$, i=k to N) in a predetermined rank range of the threshold rank k or more (that is, a rank on a lower order side including the rank k) (step 209). Here, the first filter element is a reciprocal of the value of the variance.

Specifically, a method for calculating the first filter element will be described. The filter element generation unit 35 obtains the blood flow extraction filter $P_k$ according to the equation (5) using the singular vector ($w_i$, i=k to N) included in the rank threshold value k or less, and obtains N pieces of blood flow component frame data $U\hat{}$ by multiplying the plurality of frame data 301 (N pieces of three-dimensional data U which are all of the frame data 301) by the blood flow extraction filter $P_k$ according to the equation (6). The filter element generation unit 35 calculates a variance (var $[U\hat{}]$) in the time axis direction (N direction) for corresponding pixels (position zx) of the N pieces of blood flow component frame data $U\hat{}$ according to the equation (9), and uses a reciprocal thereof as a first filter element $U_{var}$. (In the equation (9), var [ ] denotes a function for calculating a brightness variance in the time axis direction).

$$U_{var} = var[\hat{U}]^{-1} \quad (9)$$

Second Filter Element

The second filter element is calculated based on tissue component frame data obtained by multiplying one or more of frame data 301 by the singular vector $w_i$ at a predetermined rank less than the threshold rank k (steps 210 and 211). The filter element generation unit 35 uses a singular vector at a rank 1 as the singular vector at the predetermined rank less than the threshold rank k. The second filter element is a pixel value of the tissue component frame data.

Specifically, a method for calculating the second filter element will be described. The filter element generation unit 35 generates a clutter extraction filter $P_1$ according to an equation (10) based on a product of a singular vector $w_1$ and a singular value $\lambda 1$ of the first principal component from a result of the principal component analysis (step 210). The filter element generation unit 35 multiplies the clutter extraction filter $P_1$ by the N pieces of frame data 301 (three-dimensional data U), and calculates N pieces of tissue component frame data (three-dimensional data) $U_1\hat{}$ according to an equation (11).

The filter element generation unit 35 obtains frame data $U_1$ indicating a distribution of a brightness centered on the clutter component by adding and averaging pixels corresponding to the obtained N pieces of tissue component frame data (three-dimensional data) $U_1\hat{}$ in time-series in the time axis direction (N direction) according to an equation (12), and uses the frame data $U_1$ as the second filter element. (In the equation (12), avg [ ] denotes a function for calculating an average in the time axis direction (N direction).

$$P_1 = W\Lambda^{(1)}W^H = \sum_{i=1}^{1} \lambda_i w_i w_i^H \quad (10)$$

$$\hat{U}_1 = P_1 U \quad (11)$$

$$U_1 = avg[\hat{U}_1] \quad (12)$$

The image processing unit 38 weights the frame data 301 or a pixel value of an image generated based on the frame data by at least one of the first filter element $U_{var}$ and the second filter element $U_1$ to generate a clutter reducing image. Here, the image processing unit 38 weights the pixel value of the blood flow image $U_{avg}$ obtained in step 208 by the first filter element $U_{var}$ and the second filter element $U_1$ to generate the clutter reducing image.

Specifically, the mask image generation unit 36 executes weighting and adding by multiplying the first filter element $U_{var}$ and the second filter element $U_1$ by coefficients $\beta$ and $\alpha$ (an addition result of the weight coefficients $\alpha$ and $\beta$ is 1) according to an equation (13), and generates a mask image MASK (two-dimensional coefficient matrix (mask matrix)) having a reciprocal value of the weighting-added value as the pixel value (step 212). For a relationship between $\alpha$ and $\beta$, by setting the addition result thereof to 1 as described above, an advantage is present that variable parameters can be unified and an adjustment executed by a user can be simplified. However, when priority is given to an image quality, it may be effective to treat $\alpha$ and $\beta$ as independent variables, and $\alpha$ design that can be switched according to a purpose of an operator is effective.

$$MASK_{(\alpha+\beta=1)} = AVG(\alpha U_1 + \beta U_{var})^{-1} \quad (13)$$

The first filter element $U_{var}$ is a reciprocal of a brightness variance of the blood flow component frame data in the time direction (N direction) as described above. In general, the blood flow component having a three-dimensional flow has a large temporal change in the brightness as compared with a movement of the organ tissue. Therefore, by using the reciprocal of the brightness variance as a pixel value of a mask, the mask image MASK having a high numerical value (pixel value) can be generated in pixels of a tissue region of the subject 1.

On the other hand, the second filter element $U_1$ is a brightness average of the clutter component (tissue component) frame data (three-dimensional data) $U_1\hat{\,}$ extracted according to the singular vector of the first principal component. As compared to brightness data of the frame data of the receive signals, the clutter component is dominated by signals that are spatially and temporally stable, and is less susceptible to a blood flow and a noise. Therefore, by using a reciprocal of the second filter element $U_1$ as the pixel value of the mask, the mask image MASK can be generated from which a boundary and a high brightness region of the organ tissue can be selectively extracted.

In other words, the mask image generation unit 36 uses the first filter element and the second filter element, both of which show high numerical values in the tissue region that is a clutter source, and sets reciprocals thereof to mask pixel values. Therefore, the mask image MASK having an effect of reducing the clutter can be generated (step 213).

The image reconstruction unit 37 multiplies the blood flow image $U_{avg}$ generated in step 208 by the mask image MASK according to an equation (14) and executes image reconstruction to generate a highly visible blood flow image $U_{MASK}$ in which a residual clutter is small and a blood flow is emphasized (step 213).

$$U_{MASK} = U_{avg} \times \text{MASK} \tag{14}$$

The image reconstruction unit 37 can generate the blood flow image $U_{MASK}$ in which the residual clutter is small and a blood flow region is emphasized. The image reconstruction unit 37 outputs the blood flow image $U_{MASK}$ to the display processing unit 60.

On the other hand, the B mode image generation unit receives the receive beam data from the receive beamformer 22, generates a B mode image, and outputs the B mode image to the display processing unit 60.

Figure 4:
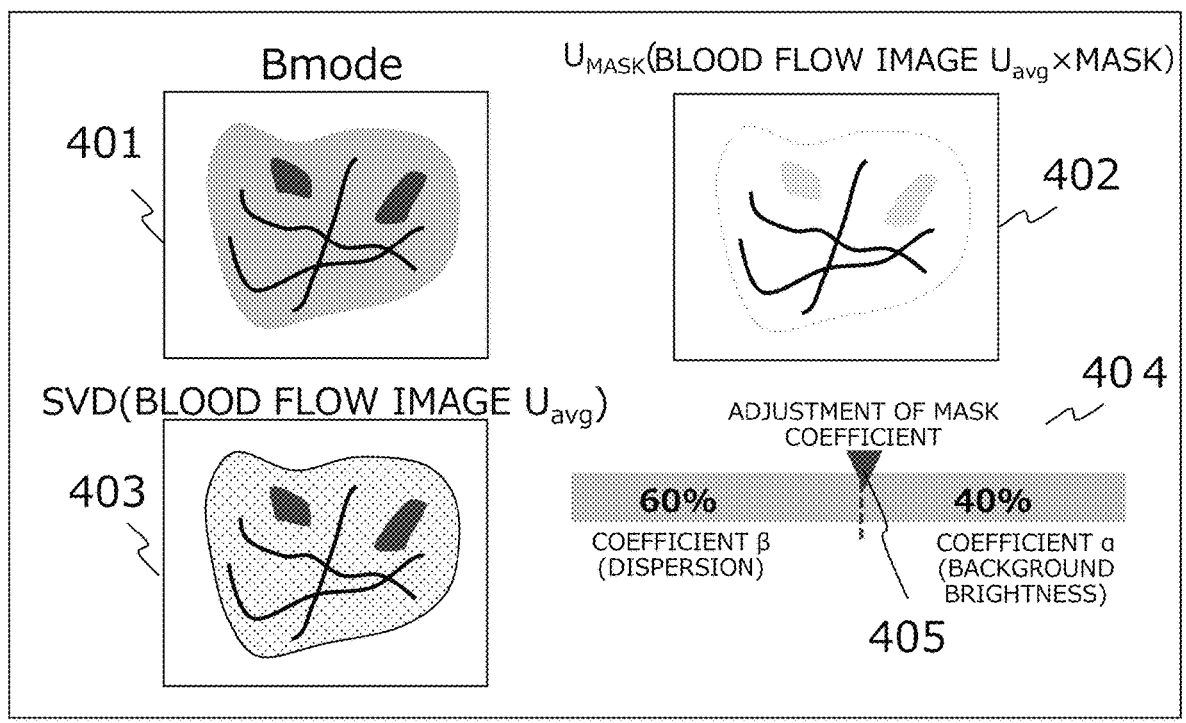
FIG. 4 is a view showing an example of a display screen of the ultrasound imaging apparatus according to the first embodiment.

For example, as shown in FIG. 4, the display processing unit 60 displays the B mode image and the blood flow image $U_{MASK}$ in which the blood flow region is emphasized in regions 401 and 402 of a screen of the display device 70, respectively. At this time, for comparison, the blood flow image $U_{avg}$ generated by the image reconstruction unit 37 in step 208 may be displayed together with a region 403.

The mask image generation unit 36 may accept, from the user, the values of the coefficients $\beta$ and $\alpha$ ($\alpha+\beta=1$) of the first filter element $U_{var}$ and the second filter element $U_1$, which are used during generating the mask image MASK according to the equation (13), on the display screen of the display device 70. For example, the display processing unit 60 causes a bar 404 in FIG. 4 to be displayed on the display screen. The user sets a ratio of the coefficient $\alpha$ and the coefficient $\beta$ by moving a mark 405 on the bar 404 left and right by the external input device 80 such as a mouse. The mask image generation unit 36 generates, in step 212, the mask image MASK using the set ratio of the coefficient $\alpha$ and the coefficient $\beta$.

A first feature according to the present embodiment is that the second filter element $U_1$ using the first principal component which is the tissue component (clutter component) is used. Accordingly, not only a low brightness region of the organ tissue but also the clutter component remaining in the high brightness region can be reduced by the mask image.

That is, since the second filter element $U_1$ is an image at a rank 1 (first principal component), the second filter element $U_1$ is an image of only a tissue (background) and does not include the blood flow component or an electrical noise. Therefore, the second filter element $U_1$ is more suitable than an original image (frame data) for removing components having a high brightness such as blood vessel walls contained in the blood flow image.

A second feature according to the present embodiment is that the first filter element $U_{var}$ using dispersion of the blood flow image $U_{avg}$ in the time direction is used. By adjusting a brightness of the blood flow image $U_{avg}$ with the mask image according to the temporal change in the brightness of the blood flow image $U_{avg}$, not only the clutter component can be reduced, but also the blood flow component can be expected to be enhanced.

That is, since the first filter element $U_{var}$ is calculated using the N pieces of blood flow component frame data $U\hat{\,}$ containing abundant blood flow components, a blood flow can be effectively extracted.

In the present embodiment, both the generation of the blood flow image $U_{avg}$ and the generation of the first and second filter elements are performed in the principal component analysis. Therefore, in order to reduce the clutter component, calculation efficiency is higher than that when processing different from the principal component analysis is performed, and a blood flow in a fine blood vessel can be highly accurately extracted in a short time. No other processing circuits are required, and a device configuration can be simplified.

Second Embodiment

An ultrasound imaging apparatus according to a second embodiment will be described. The ultrasound imaging apparatus according to the second embodiment has the same configuration as the apparatus according to the first embodiment, but further has a function of appropriately setting coefficients $\beta$ and $\alpha$ ($\alpha+\beta=1$) to be multiplied by the first filter element $U_{var}$ and the second filter element $U_1$. That is, the image processing unit 38 calculates a similarity of the plurality of frame data 301, and sets the weighting coefficients $\alpha$ and $\beta$ based on a calculation result.

When a correlation (similarity) between the N pieces of frame data 301 for executing a principal component analysis is high, it is appropriate that the coefficients $\beta$ and $\alpha$ are both around 0.5. This is because a clutter component and a blood flow component can be effectively separated according to the principal component analysis when the correlation (similarity) between the N pieces of frame data 301 is high, and a brightness of the clutter component is also high in the calculation result of the second filter element $U_1$. Accordingly, the mask image MASK obtained by taking a reciprocal after weighting and adding the first filter element $U_{var}$ and the second filter element $U_1$ is generated, and is multiplied by the blood flow image $U_{avg}$, thereby achieving a clutter reducing effect.

On the other hand, when the correlation of the N pieces of frame data 301 is low, it is assumed that the clutter component is present across a plurality of principal components and a brightness of the clutter component of the second filter element $U_1$ is low. When the mask image MASK is configured in step 212 in this state, a phenomenon may occur in which the clutter component of the blood flow image $U_{avg}$ is rather emphasized by multiplying the blood flow image MASK by the blood flow image $U_{avg}$.

In order to avoid this phenomenon, when the correlation between the N pieces of frame data 301 is low, a method of setting a value of the coefficient α to be low to reduce a contribution ratio of the second filter element $U_1$ to the mask image MASK is effective.

Figure 5:
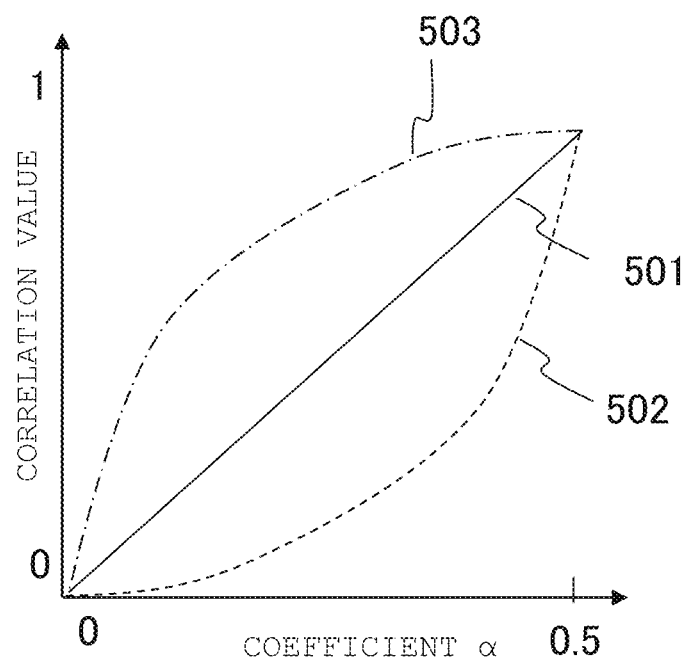
FIG. 5 is a graph showing a relationship between a correlation value (similarity) of a plurality of frame data calculated by an ultrasound imaging apparatus and a coefficient α of a second filter element according to a second embodiment.

For example, as shown in FIG. 5, a linear graph 501 and curve graphs 502 and 503 are set such that the coefficient α of the second filter element $U_1$ becomes smaller as the correlation value of the N pieces of frame data 301 becomes lower, and are stored in the memory 40.

Figure 6:
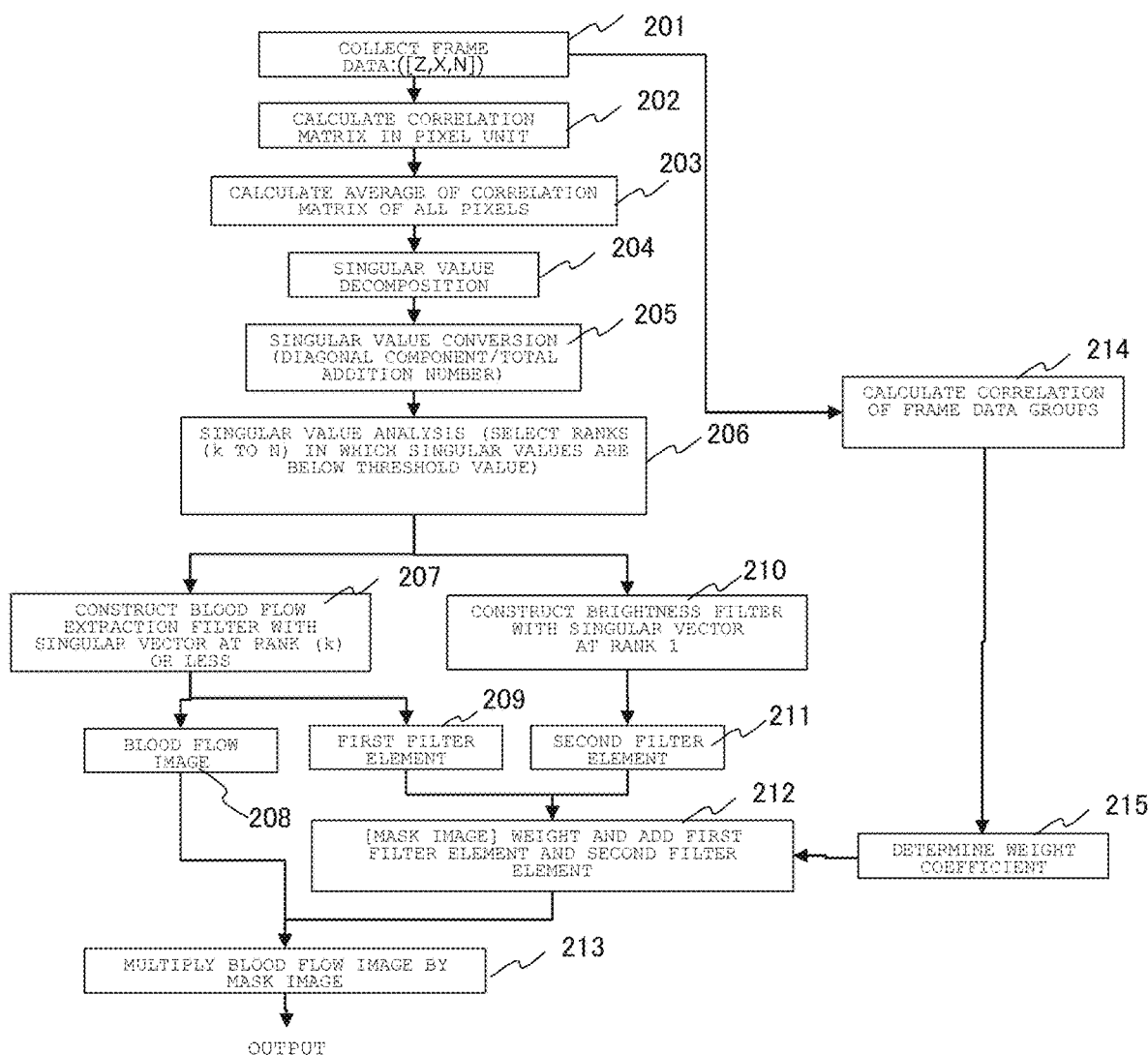
FIG. 6 is a flowchart showing processing executed by the blood flow image generation unit 30 of the ultrasound imaging apparatus according to the second embodiment.

As shown in a flow in FIG. 6, the mask image generation unit 36 executes steps 214 and 215 to calculate the correlation value of the N pieces of frame data 301, and obtains the coefficient α corresponding to the calculated correlation value based on any of the graphs 501, 502, and 503 in FIG. 5. Then, in step 212, the second filter element $U_1$ and the first filter element $U_{var}$ are weighted using the obtained coefficient α and β $(=1-\alpha)$ according to the equation (13) to obtain the mask image MASK.

Accordingly, the appropriate coefficient α can be automatically set in the ultrasound imaging apparatus.

As shown in FIGS. 7A and 7B, a graph 1001 showing a temporal change (stability of data) of the correlation value calculated in step 214 may be displayed on the display device 70 together with the blood flow image $U_{avg}$ after reducing a residual clutter generated in step 213. FIG. 7A shows a case in which the correlation value is maintained high and the stability of the data is high, and the coefficient α is set to a large value close to 0.5. On the other hand, FIG. 7B shows a case in which the correlation value is maintained low and the stability of the data is low, and a ratio of the coefficient α is set to be small.

A calculation of the correlation value of the N pieces of frame data 301 in step 214 uses a generally known similarity calculation method such as a cross-correlation calculation.

In the flow in FIG. 6, steps other than the above steps is the same as those in the flow in FIG. 2 according to the first embodiment, and thus a description thereof will be omitted.

Figure 8:
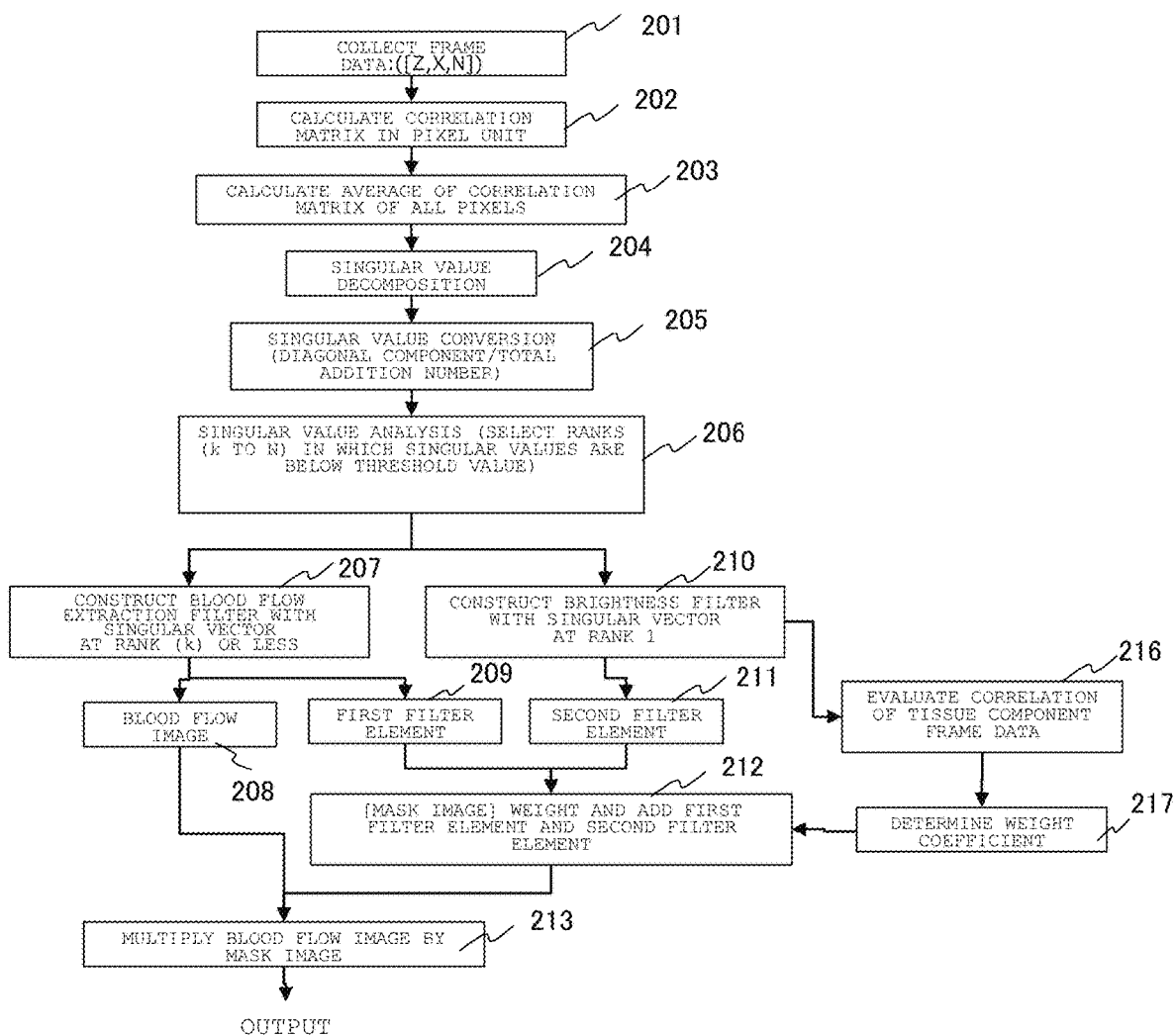
FIG. 8 is a flowchart showing another example of the processing executed by the blood flow image generation unit 30 of the ultrasound imaging apparatus according to the second embodiment.

As shown in a flow in FIG. 8, the mask image generation unit 36 can also determine the similarity of the N pieces of frame data 301 using the tissue component frame data $(U_1\hat{\,})$ obtained using a first principal component.

The tissue component frame data is a component (three-dimensional data) mainly including a tissue structure extracted according to a singular vector of the first principal component. As described above, signals reflected from a living body mainly include a component from organ tissues, and a component from a blood flow is 10% to 1% or less. That is, the similarity of the data is appropriate for judging mainly the component of the organ tissue.

Accordingly, the mask image generation unit 36 executes steps 216 and 217 before step 212 to calculate the correlation value of the tissue component frame data, and obtains the coefficient α corresponding to the calculated correlation value based on the graph in FIG. 5.

By calculating the correlation value of the N pieces of frame data 301 using the tissue component frame data, an influence of a tissue movement and a noise that affect the principal component analysis can be eliminated, and the correlation can be determined more effectively. Accordingly, the appropriate coefficient α can be automatically set in the ultrasound imaging apparatus. Here, α and β are treated as dependent variables (α+β=1). However, this limitation is a setting that focuses on convenience of an operation, and does not limit the treating of α and β as independent variables (that is, 0<=α<=1 and 0<=β<=1) while maintaining the described apparatus form.

In the flow in FIG. 8, steps other than the above steps is the same as those in the flow in FIG. 2 according to the first embodiment, and thus a description thereof will be omitted.

A configuration, an operation, and an effect of the ultrasound imaging apparatus according to the second embodiment other than those described above are the same as those according to the first embodiment, and thus a description thereof will be omitted.

Third Embodiment

An ultrasound imaging apparatus according to a third embodiment will be described. The ultrasound imaging apparatus according to the third embodiment has the same configuration as the apparatus according to the first embodiment, but further has a function of determining a correlation (similarity) between the N pieces of frame data 301 and adjusting an acquired number of the data.

When the number N of the frame data 301 used for a principal component analysis is large in the matrix conversion unit 32, the matrix analysis unit 33, the singular value analysis unit 34, and the filter element generation unit 35, the number of distinguished principal components increases and accuracy of separation between a clutter and a blood flow increases. However, a calculation load in the blood flow image generation unit 30 is heavy, which may lead to a decrease in a frame rate.

Therefore, in the third embodiment, when the correlation between the frame data 301 is sufficiently high, both effects of reducing the clutter and improving the frame rate are achieved by reducing the acquired number N.

Figure 9:
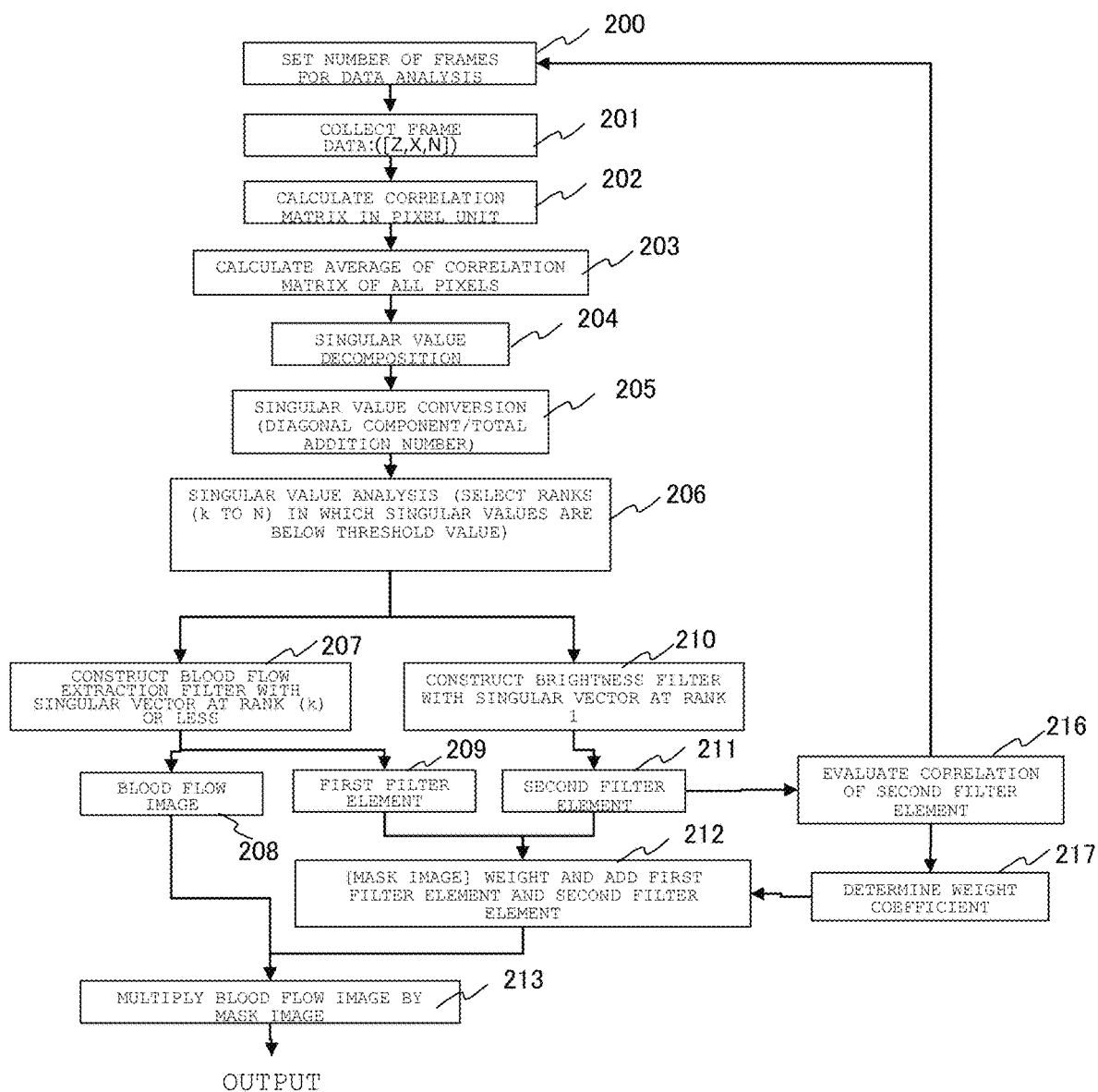
FIG. 9 is a flowchart showing processing executed by the blood flow image generation unit 30 of an ultrasound imaging apparatus according to a third embodiment.

Specifically, as shown in a flow in FIG. 9, step 200 of setting the number N of the frame data 301 to be collected is executed before step 201 of collecting the N pieces of frame data 301.

Figure 10:
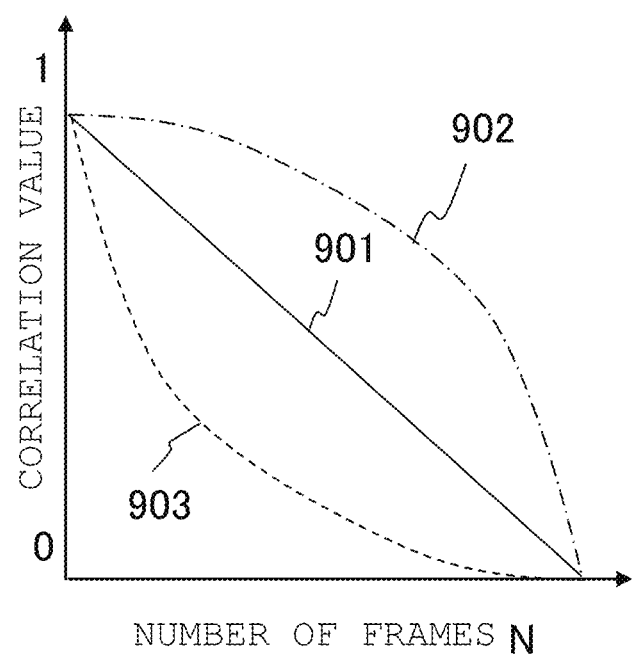
FIG. 10 is a graph showing a relationship between a correlation value (similarity) of a plurality of frame data calculated by the ultrasound imaging apparatus and the number of frame data to be collected according to the third embodiment.

In step 200, a correlation value of tissue component frame data calculated in previous step 216 is received, and the appropriate number N of frames is set according to, for example, a graph 901, 902 or 903 showing a relationship between a predetermined correlation value and the number of frames as shown in FIG. 10. The correlation value of the tissue component frame data corresponds to a correlation value of the N pieces of frame data 301 as described in the second embodiment.

As shown in FIG. 10, the linear graph 901 and the curve graphs 902 and 903 are set such that the higher the correlation value of the N pieces of frame data 301, the smaller the number N of frames to be acquired. These graphs 901 to 903 are stored in the memory 40.

By using the flow in FIG. 9, the number N of the frame data 301 used for the current principal component analysis can be set to an appropriate number using the correlation value of the tissue component frame data calculated in previous step 216.

As a method for calculating the correlation value of the N pieces of frame data 301, in addition to the method of calculating the correlation value of the tissue component frame data, the correlation value may be calculated directly based on the frame data 301 in step 214 of the flow in FIG. 6.

If the value of the appropriate number N of frames changes significantly each time the principal component analysis is executed, a brightness flicker occurs at a timing of switching a displayed blood flow image, which may impair visibility as a moving image. In order to prevent the brightness flicker, it is effective to provide a limiting measure in which, for example, a fluctuation of the number of data between consecutive frames is 2 frames or less.

A configuration, an operation, and an effect of the ultrasound imaging apparatus according to the third embodiment other than those described above are the same as those according to the first embodiment and the second embodiment, and thus a description thereof will be omitted.

What is claimed is:

1. An ultrasound imaging apparatus comprising:
   a data collection unit that receives a plurality of receive signals obtained by receiving, with an array in which a plurality of transducers are arranged in an x direction, ultrasound waves reflected sequentially in a depth z direction of a subject to which the ultrasound waves are transmitted, that repeats processing of generating frame data by arranging the receive signals on a zx plane, and that generates the frame data for N frames;
   a matrix conversion unit that generates a correlation matrix based on a vector in which data at a corresponding position zx of the frame data is arranged for N frames;
   a matrix analysis unit that performs singular value decomposition of the correlation matrix and that calculates a singular value and a singular vector for each of N ranks of the receive signals;
   a filter element generation unit that generates at least one of a first filter element and a second filter element as a filter element; and
   an image processing unit that uses the filter element generated by the filter element generation unit to weight the frame data or a pixel value of an image generated based on the frame data and generate a clutter reducing image, wherein
   the filter element generation unit generates the first filter element based on a variance between data at the corresponding position zx among a plurality of blood flow component frame data obtained by multiplying a plurality of the frame data by a plurality of singular vectors in a predetermined rank range of a preset threshold rank k or more, respectively, and
   the filter element generation unit generates the second filter element based on tissue component frame data obtained by multiplying one or more of the frame data by a singular vector at a predetermined rank less than the threshold rank k.

2. The ultrasound imaging apparatus according to claim 1, wherein
   the first filter element is a reciprocal of a value of the variance.

3. The ultrasound imaging apparatus according to claim 1, further comprising:
   an image reconstruction unit that reconstructs a blood flow image which is extracted a blood flow component, wherein
   the image reconstruction unit generates the blood flow image in which data obtained by averaging a plurality of blood flow component frame data for each position zx is used as a pixel value, the plurality of blood flow component frame data being obtained by using a plurality of singular vectors in a predetermined rank range of the threshold ranks k to N as a blood flow extraction filter and multiplying a plurality of the frame data by the plurality of singular vectors, and
   the image processing unit weights the pixel value of the blood flow image by at least one of the first filter element and the second filter element to generate the clutter reducing image.

4. The ultrasound imaging apparatus according to claim 3, wherein
   the image processing unit generates a mask image in which a pixel value is a value obtained by multiplying the first filter element and the second filter element by a weighting coefficient and adding and averaging products thereof for each position zx, and generates the clutter reducing image by multiplying a pixel value of the mask image at a position corresponding to the pixel value of the blood flow image.

5. The ultrasound imaging apparatus according to claim 4, wherein
   a sum of a weight coefficient of the first filter element and a weight coefficient of the second filter element is 1.

6. The ultrasound imaging apparatus according to claim 4, wherein
   the image processing unit calculates a similarity of the plurality of frame data, and sets the weight coefficient based on a calculation result.

7. The ultrasound imaging apparatus according to claim 6, wherein
   the image processing unit calculates the similarity of the plurality of frame data by calculating a similarity of the tissue component frame data.

8. An ultrasound imaging apparatus comprising:
   a data collection unit that receives a plurality of receive signals obtained by receiving, with an array in which a plurality of transducers are arranged in an x direction, ultrasound waves reflected sequentially in a depth z direction of a subject to which the ultrasound waves are transmitted, that repeats processing of generating frame data by arranging the receive signals on a zx plane, and that generates the frame data for N frames;
   a matrix conversion unit that generates a correlation matrix based on a vector in which data at a corresponding position zx of the frame data is arranged for N frames;
   a matrix analysis unit that performs singular value decomposition of the correlation matrix and that calculates the singular value and a singular vector for each of N ranks of the receive signals;
   a filter element generation unit that generates at least one of a first filter element and a second filter element as a filter element; and
   an image processing unit that uses the filter element generated by the filter element generation unit to weight the frame data or a pixel value of an image generated based on the frame data and generate a clutter reducing image, wherein
   the first filter element is calculated based on a variance between data at the corresponding position zx among a plurality of blood flow component frame data obtained by multiplying a plurality of the frame data by a plurality of singular vectors in a predetermined rank range of a preset threshold rank k or more, respectively,
   the second filter element is calculated based on tissue component frame data obtained by multiplying one or more of the frame data by a singular vector at a predetermined rank less than the threshold rank k,
   the ultrasound imaging apparatus further comprises an image reconstruction unit that reconstructs a blood flow image which is extracted a blood flow component,
   the image reconstruction unit generates the blood flow image in which data obtained by averaging a plurality of blood flow component frame data for each position zx is used as a pixel value, the plurality of blood flow component frame data being obtained by using a plurality of singular vectors in a predetermined rank range of the threshold ranks k to N as a blood flow extraction filter and multiplying a plurality of the frame data by the plurality of singular vectors, the image processing unit weights the pixel value of the blood flow image by at least one of the first filter element and the second filter element to generate the clutter reducing image, the image processing unit generates a mask image in which a pixel value is a value obtained by multiplying the first filter element and the second filter element by a weighting coefficient and adding and averaging products thereof for each position zx, and generates the clutter reducing image by multiplying a pixel value of the mask image at a position corresponding to the pixel value of the blood flow image, and the data collection unit calculates a similarity of the plurality of frame data, and sets, based on a calculation result, a number N of the frame data to be collected.

9. The ultrasound imaging apparatus according to claim 1, wherein
the filter element generation unit calculates the first filter element using a plurality of singular vectors in a rank range from the threshold rank k to a rank N as a blood flow component filter.

10. The ultrasound imaging apparatus according to claim 1, wherein
the filter element generation unit generates the second filter element using a singular vector at a rank 1 as the singular vector at the predetermined rank less than the threshold rank k.

11. The ultrasound imaging apparatus according to claim 1, wherein
the matrix conversion unit obtains correlation matrices for a plurality of positions zx, and obtains an average correlation matrix of the correlation matrices, and
the matrix analysis unit calculates the singular value and the singular vector based on the average correlation matrix obtained by the matrix conversion unit.

12. The ultrasound imaging apparatus according to claim 1, further comprising:
a singular value analysis unit that analyzes the singular value and that calculates the threshold rank k.

13. A signal processing method comprising:
a data collection step of receiving a plurality of receive signals obtained by receiving, with an array in which a plurality of transducers are arranged in an x direction, ultrasound waves reflected sequentially in a depth z direction of a subject to which the ultrasound waves are transmitted, repeating processing of generating frame data by arranging the receive signals on a zx plane, and generating the frame data for N frames;
a matrix conversion step of generating a correlation matrix based on a vector in which data at a corresponding position zx of the frame data is arranged for N frames;
a matrix analysis step of performing singular value decomposition of the correlation matrix and calculating the singular value and a singular vector for each of N ranks of the receive signals;
a filter element generation step of generating at least one of a first filter element and a second filter element as a filter element; and
an image processing step of using the filter element generated by the filter element generation unit to weight the frame data or a pixel value of an image generated based on the frame data and generate a clutter reducing image,
in the filter element generation step, the first filter element being generated based on a variance between data at the corresponding position zx among a plurality of blood flow component frame data obtained by multiplying a plurality of the frame data by a plurality of singular vectors in a predetermined rank range of a preset threshold rank k or more, respectively, and
in the filter element generation step, the second filter element being generated based on tissue component frame data obtained by multiplying one or more of the frame data by a singular vector at a predetermined rank less than the threshold rank k.

14. A non-transitory computer readable medium comprising executable instructions to cause a computer to perform a signal processing method comprising:
a data collection step of receiving a plurality of receive signals obtained by receiving, with an array in which a plurality of transducers are arranged in an x direction, ultrasound waves reflected sequentially in a depth z direction of a subject to which the ultrasound waves are transmitted, repeating processing of generating frame data by arranging the receive signals on a zx plane, and generating the frame data for N frames;
a matrix conversion step of generating a correlation matrix based on a vector in which data at a corresponding position zx of the frame data is arranged for N frames;
a matrix analysis step of decomposing the correlation matrix into a singular value and calculating the singular value and a singular vector for each of N ranks of the receive signals;
a filter element generation step of generating at least one of a first filter element and a second filter element as a filter element; and
an image processing step of using the filter element generated by the filter element generation unit to weight the frame data or a pixel value of an image generated based on the frame data and generate a clutter reducing image,
in the filter element generation step, the first filter element being generated based on a variance between data at the corresponding position zx among a plurality of blood flow component frame data obtained by multiplying a plurality of the frame data by a plurality of singular vectors in a predetermined rank range of a preset threshold rank k or more, respectively and
in the filter element generation step, the second filter element being generated based on tissue component frame data obtained by multiplying one or more of the frame data by a singular vector at a predetermined rank less than the threshold rank k.

* * * * *